United States Patent [19]

Penalva et al.

[11] Patent Number: 4,753,877
[45] Date of Patent: Jun. 28, 1988

[54] CEPHALOSPORIUM ACREMONIUM

[76] Inventors: Miguel A. Penalva; Angeles Tourino; Cristina Patino; Florentina Sanchez; Victor Rubio; Jose M. Fernandez-Sousa, all c/o Antibiotics S.A., Bravo Murillo 38, 28015 Madrid, Spain

[21] Appl. No.: 795,873

[22] Filed: Nov. 7, 1985

[30] Foreign Application Priority Data

Nov. 7, 1984 [GB] United Kingdom ............ 8428094
Feb. 11, 1985 [GB] United Kingdom ............ 8503441
Mar. 29, 1985 [GB] United Kingdom ............ 8508353

[51] Int. Cl.$^4$ .................. C12Q 1/04; C12N 15/00; C12N 1/14; C12R 1/75
[52] U.S. Cl. ........................... 435/34; 435/172.3; 435/254; 435/926; 435/320; 935/34; 935/68; 935/84
[58] Field of Search .......... 435/34, 284, 317, 926, 435/172.3; 935/34.27, 68, 60, 84, 61, 14; 536/27

[56] References Cited
FOREIGN PATENT DOCUMENTS 0135895 8/1984 Japan .................. 435/926

OTHER PUBLICATIONS

Ammerer, (1983), in Methods In Enzymology vol. 101, pp. 192-201.
Ball et al., (1982), Chemical Abstracts, vol. 96, No. 25, p. 582, item #215984s.
Kang et al., (1973), Chemical Abstracts, vol. 78, No. 16, p. 170, item #107508j.
Kang et al., (1973), Chemical Abstracts, vol. 78, No. 16, p. 180, item #107610m.
Hitzeman et al., (1981), Nature, vol. 293, pp. 717-722.
Skatrund et al. (1984), Current Genetics, vol. 8, pp. 155-163.
Vankov et al., (1982), Current Genetics, vol. 5, pp. 153-155.
Thompson et al., (1983), Proceedings Of The National Academy of Science, vol. 80, pp. 5190-5194.
Cuot et al., (1983), Gene, vol. 23. pp. 331-341.
Jímenez et al., (1980), Nature, vol. 287, pp. 869-872.
Scott et al., (1983), Cell, vol. 34, pp. 557-567.
Beck et al., (1982), Gene, vol. 19, pp. 327-336.
Oka et al., (1981), Journal of Molecular Biology, vol. 147, pp. 217-226.

Primary Examiner—Esther M. Kepplinger
Assistant Examiner—William J. Herald
Attorney, Agent, or Firm—Saidman, Stern, Kessler & Goldstein

[57] ABSTRACT

The provision of Cephalosporium acremonium resistant to the aminoglycoside G418 allows the use of this aminoglycoside as a marker to select aminogylcoside-resistant cells of Cephalosporium acremonium from non-resistant cells of Cephalosporium acremonium. Aminoglycoside resistance can be imparted by transformation of Cephalosporium acremonium with a suitable vector.

7 Claims, 6 Drawing Sheets

A - Ava II
B - Bam HI
H - Himd III
P - Pst I
R - EcoRI
X - xho I

FIG.5a.

```
CTGCAGCACTATTCTTATATATTGTTTATTCACAATTAGTAGAAGGAAAAGTTGCAGATAGAAATCCTTGAATGACTCCG
GACGTCGTGATAAGAATATATAACAAATAAGTGTTAATCATCTCTTTCAACGTCTATCTTTAGGAACTTACTGAGGC

GGATTCTATACTGATATTTTACAAGCTAATTTGAATAGATATTATAATAGTTTAGAATGAGGGTTATCTAGTCCTCTAA
CCTAAGATATGACTATAAAATGTTCGATTAAACTTATCTATAATATTATCAAATCTTACTCCCAATAGATCAGGAGGATT

ACCTCATGCATTTGTAAGTTACCTAAACAAGTAGAGGGTTTTAAGTTTAGAATAATGATTAATTACTAATACTAAATACA
TGGAGTACGTAAACATTCAAATGGATTTGTTTCATCTCCCAAAATTCAAATCTTATTACTAATTATGATAGGATTTATGT

AGTCTCATTAGCTCAATTGGTAGAGCATAATACTTCTAATATTTGTATCCTAGTTCGAATCTAGGATGAGATTTAATACG
TCAGAGTAATCGAGTTAACCATCTCGTATTATGAAGATTATAAACATAGGATCAAGCTTAGATCCTACTCTAAATTATGC

AGACAATCTTTTCTAAAATAAATTGCCTATTGAAGTCTTTTGGCTGTTTTTGGTTTAATATATGATAAAT
TCTGTTAGAAAAGATTTTATTTAACGGATAACTTCAGAAACCGACAAAAACGCAATAAAAACCAAATTATATACTATTTA

AAAAAATAAAGCTAATAAACCTTAATGAATTTCTTTTTGTTCATTAATAGAAATATTCAAGATTACTACAACTAAAAT
TTTTTTATTTCGATTATTTGGAATTACTTAAAAGAAAACAAGTAATTATCTTTATAAGTTCTAATGATGTTGATTTTA

AAATATATTTTTATAATAAGTTATTATTAACTAATGATTTCTATTCTAGAAAATCTTATATTAATGCTTCCTGCTCTTTTAGTAGTAG
TATTTAATACTAAAAGTATCATGTTACTAAAGATCTTTTAGAATATAATTACGAAGGACGAGAAAATCATCATC

CTTATGTTACAGTAGCAGAAAGAAAAACTATGGCTAGTATGCAAAGAAGATTAGGACCTAATGCTGTGTAGGTTATTATGGT
GAATACAATGTCATCGTCTTCTTTTGATACCGATCATACGTTTCTCTAATCCTGGATTACGACATCCAATAATACCA

TTATTACAAGCTTTTGCTGATGCCTTAAAACTAATATTAAAAGAAATATGTAGCACCGACTCAAGCTAATATATTCTATT
AATAATGTTCGAAAACGACTACGGAATTTTGATTATAATTTTCTTATACATCGTGGCTGAGTTCGATTATAATAAGATAA

TTTCTTAGGACCAATAGTAACACTGGTATTTGCTTTATTAGGTTATGCAGTAATTCCTTATGGTCCCGGTTTATCTTTAA
AAAGAATCCTGGTTATCATTGTGACCATAAACGAAATAATCCAATACGTCATTAAGGAATACCAGGGCCAAATAGAAATT

GTGACATGGAATTAGGAATATTATTTATGTTAGCAGTTTCATCTCTTTACTCTACTTATGTATTTTACTTGCAGGATGAAGT
CACTGTACCTTAATCCTTATAATAATACAATCGTCAAGTAGAAATCGATGAATACCATAAAATGAACGTCCTACTTCA

GCTAATAGTAAATACGCTTTTTAGGATCTTTAAGAAGTACTGCTCAATTAATTAGTTATGAGCTAGTATTAAGTTCCGT
CGATTATCATTTATGCGAAAAAATCCTAGAAATTCTTCATGACGAGTTAATTAATCAATACTCGATCATAATTCAAGGCA
```

FIG. 5b.

```
TTTATTGATTATTATTATATTGATAACTAATAGTTTAAATTTAAATGTCAATTTCAAAAAATTATTTGATTAGCTT
AAATAACTAATAATAATACTATTGATTATCAAATTTAAATTTACAGTTAAGTTTTTAATAAACTAATCGAA

TACCATTATTATGTATATTAATAATATTTTTATAGGTTCTGTAGCTGAAACAAATAGAGCTCCTTTTGATTAGCCGAA
ATGGTAATAATACATATATTATTTATAAAAATATCCAAGACATCGACTTTGTTTATCTCGAGAAAACTAAATCGGCTT

GCTGAATCGGAGTTAGTGGATTTATGACAGAACATGCTGCTGTTATATTTGTTTCTTTTTTTGGCGGAATGC
CGACTTAGCCTCAATCAATCACCTAAATACTGTCTTGTACGACGACAATATAAACAAAAGAAAAAAACCGCCTTATACG

TAGTATAGTACTAATGTGTATTTAACTAGTATTTATTTTAGGTGGTTATTTAATAGAATTTGATTATTCATATTTAT
ATCATATCATGATTACACATAAAATTGATCATAAAAATCCACCAATAAAATTATCTTAAACTAATAAGTATAAATA

TATATAATTACTATTATTTGATATTGGGTCTTCTTACAGTTTAATGAGAAGAATTATTAAATAGTACATCTTTCAAT
ATATATTAATGATAATAAAACTATAACCCAGAAGAATGTCAAATTACTCTCTTAATAATTTATCATGTAGAAAGTTA

GGTCTTTTGACTAGTATTACTTTAGGTATAAAAACTTCAGCCATGGTATTTATATTTATTTGAGTAAGAGCCTCTTTCCC
CCAGAAAACTGATCATAATGAAATCCATATTTTGAAGTCGGTACCATAAATAAATAAACTCATTCTCGGAGAAGGG

TCGAATTCGTTTTGATCAATTAATGTCATTTTGTTGAACGGTTTACTCATTGTTATCACCGATATTATTTGGGTTCCTTATTTAATTC
AGCTTAAGCAAAACTAGTTAATTACAGTAACAACTTGCCAAATGATGGCTATAATAAACCCAGGAATAAAATTAAG

CTTCTTACTTTATACCTTCGGTATGTGTTTTTTTTGTCGCTTACATAAAGACAAATACTCTTGTTAAAAATAAAGAGC
GAAGAAATGAAATATGGAAGCCATACAAAAAAACAGCGAATGTATTTCTGTTTATGAGAACAATTTTTATTTCTCG

GTGTTATCCTAATTTTGTGAAGTTGCTTTTGCTTTTGAAATTTTAACCTTGAAATTTTCCGAGAATATTTTAGAATATATAAATATTGTTC
CACAATAGGATTAAAACACTTCAAACGAAAAATTGGAACTTTAAAAGGCTCTTATAAAATCTTATATATATTATAACAAG

ATTTGATTAAAATTCTTAAATAGTCAAAAATTAAGCACTAAAAGAATGTTTAGCACTACACCCCGATACGTCATGCGATACCC
TAAACTAATTAAGAATTTATCAGTTTTATCGTGATTTTCTTACAAATCGTGATGGGCTATGCAGTACGGCTATGGG

ACAGGTGGAGCTGAAGTAGAACTAGCCCTAATTCTATATGCGATTCCCGTCAGTTCTATGTTTTTATGGCCATCGTCTG
TGTCCACCTCGACTTCATCTTTGATCGGGATTAAGATATACGCTAAGGGCAGTCAAGATACAAAAAATACCGGTAGCAGAC

AGCTACAGTTACTATAGCTGCAG
TCGATGTCAATGATATCGACGTC
```

CEPHALOSPORIUM ACREMONIUM

BACKGROUND OF THE INVENTION

The present invention relates to the eukaryote *Cephalosporium acremonium*. This microorganism is used on a large scale in the initial step for production of a range of semi-synthetic cephalosporin antibiotics.

More particularly, but not exclusively, the present invention relates to the application of recombinant DNA techniques to the genetic engineering of *C. acremonium*. Although recent developments in recombinant DNA techniques have led to considerable advances in industrial microbiology, many of these developments have been concerned with prokaryotic organisms and not with eukaryotic organisms.

OBJECT OF THE INVENTION

Development of techniques for greater understanding of the eukaryotic microorganism *C. acremonium* are required as part of the need to develop improved strains for industrial use, especially for enhanced antibiotic production.

SUMMARY OF THE INVENTION

According to the present invention, there is provided *Cephalosporium acremonium* with an aminoglycoside resistance marker.

*C. acremonium* has been believed uneffected by aminoglycoside antibiotics, due to the impermiability of the cell wall to this class of compounds. We have now determined that *C. acremonium* is sensitive to the aminoglycoside antibiotic G418 at concentrations, for example, of around 50 ug/ml. This sensitivity opens up the possibility of genetic development based on the use of a G418 resistance gene as a dominant marker in *C. acremonium*.

*Cephalosporium acremonium* of this invention can be obtained by the use of a vector also provided by the present invention. The vector is capable of transforming *C. acremonium* to G418 resistance.

PREFERRED EMBODIMENTS

The aminoglycoside employed in this invention is preferably one inactivated by an aminoglycoside 3'-phosphotransferase ["APH(3')"]. Several different APH(3') enzymes are known, for example:

Type I of transposon Tn601(903) [A Jimenez et al., *Nature*, 287 (1980), 869, and also A Oka et al., *Journal of Molecular Biology*, 147 (1981), 217];

Type II of transposon Tn5 [E Beck et al., *Gene*, 19 (1982), 327], and,

The APH(3') of *Streptomyces fradiae* [C J Thompson et al., *Proc. Natl. Acad. Sci.*, 80 (1983), 5190].

Any of these types may be employed, though type I is currently preferred. All of these enzymes confer aminoglycoside resistance and show sequence homology, indicating that they possibly arise from a common evolutionary origin.

As a corollary, the aminoglycosides inactivated by APH(3') enzymes show structural similarities and apart from a phosphorylatable 3'-hydroxy group they also are typically 4,5- or 4,6-disubstituted. Examples of such aminoglycosides which can be used to select resistant bacterial cells include not only G418 but also neomycins B and C, kanamycins A, B and C, paromomycins I and II, and gentamycins A and B. Typically the aminoglycoside will be G418 or a neomycin. With *C. acremonium* only G418 is used for selection.

The aminoglycoside resistance imparted by phosphotransferase activity can be achieved using vectors with suitable gene sequences, such as occur for example in the transposons Tn903 or Tn5, or in *S. fradiae*, as mentioned above.

The signals for gene expression are different in prokaryotic and eukaryotic systems, and for preference, the gene coding for aminoglycoside resistance can be manipulated to be under the control of a eukaryotic promoter, for example the promoter of *Saccharomyces cerevisiae* is alcohol dehydrogenase I gene (ADCI). The use of ADC I promoter or any other fungal or eukaryotic promoter to increase the expression of the aminoglycoside resistance gene in transformants of *C. acremonium* offers the possibility of a higher resistance to give an easier and cleaner selection of transformants.

In the present invention a prokaryotic gene is transcribed from a eukaryotic promoter with no ATG triplets between the respective starts of transcription and translation. It is believed that in addition to differences in promoter sequence, eukaryotic genes are usually devoid of ATG triplets (i.e. AUG in the mRNA, coding for initial methionine) between the respective starts of transcription and translation. An absence of ATG triplets in this region could promote efficient gene expression.

Vectors of this invention can usefully also include an autonomous replication sequence, ars, particularly an ars from mitochondrial DNA of *C. acremonium*.

In one aspect, the present invention extends to nucleic acid sequences substantially functionally homologous with plasmid pMA4 deposited in *E. coli* at the National Collection of Industrial and Marine Bacteria on Nov. 1, 1984 under the accession number NCIB 12025. For example, the invention embraces any other plasmid which exhibits substantial functional homology with pMA4, for instance any plasmid which can hybridize up to 80% with the plasmid in NCIB 12025. The deposit was made under the provisions of the Buadapest Treaty, and samples are available under the relevant provisions of the appropriate regulations.

Plasmid pMA4 is a 6.8 Kb chimeric plasmid including a fragment of the transposon Tn903 coding for APH(3') activity, and can be used for the successful transformation of *C. acremonium* spheroplasts. The plasmid pMA4 can also be used to transform bacteria, such as *E. coli* HB101 or *E. coli* DH1. For instance, the resistance gene can be excised from pMA4 and manipulated to get an EcoRI fragment devoid of ATG triplets as mentioned above and inserted into a known plasmid, such as pAAR6, which contains the DNA sequence "ADCI promoter-APH(3') gene-ADCI terminator". This sequence can then be excised and employed as the basis for further developmental constructions, for example in conjunction with an autonomous replication sequence and/or at least one phenotypic marker. Clearly, the construction of this cassette fragment, whether as a vector or not, provides a basis for the use of other promoters and other genes in *C. acremonium*.

The plasmid pMA4 contains single BamH I and Sal I sites and can be useful for the introduction of genes in *C. acremonium* that can give rise to high-titre cephalosporium producers or to cephalosporin strains able to produce a hybrid antibiotic.

In using the vectors of this invention, transformation of *C. acremonium* spheroplasts is conveniently effected by a novel method of this invention for the transformation of *C. acremonium*, in which cultivated mycelial growth of *C. acremonium* is subjected to the action of zymolase 20T (Miles) or equivalent and lytic enzyme L1 (BDH) or equivalent.

While the invention has been described above by reference to the products of the genetic engineering processes used to obtain the DNA sequences, vectors and transformed strains which comprise the present invention, it should be understood that the invention also extends to the product(s) of the genes employed.

EXAMPLES OF THE INVENTION

The present invention is illustrated by the following non-limiting example in which reference is made to the drawings, wherein;

FIGS. 5a and 5b, shows a portion of the nucleotide sequence including the ars locus, as utilized in plasmids pFS1 and pFS2.

EXAMPLE 1

Formation of Spheroplasts

*Cephalosporium acremonium* ATCC 11550 was grown in a defined medium (Hamlyn et al., Enzyme Microb. Technol., 3, (1981) 321) for two days at 28° C. Mycelium was recovered by filtration and washed with sterile water. 1 gram (wet weight) of mycelium was suspended in 10 ml of 0.2M McIlvaine's buffer, pH 7.3, containing 0.5M β-mercaptoethanol, and was incubated for 15 minutes at 30° C. Mycelium was recovered and 0.5 g wet weight was suspended in 5 ml lytic mixture [zymolase 20T (Miles) 20 mg/ml, lytic enzyme L1 (BDH) 20 mg/ml in 1M sorbitol] and incubated for 6 hours at 30° C.

Spheroplasts were purified from mycelial debris by layering on a 1M MgSO$_4$ cushion. The spheroplast suspension was diluted 10-fold with 1M sorbitol, centrifuged, washed with 1M sorbitol and resuspended in 10 ml of 1M sorbitol, 10 mM CaCl$_2$, 10 mM Tris-HCl pH 8.0 (STC), ready for transformation.

EXAMPLE 2

General Procedure for Transformation

Plasmid Regeneration Medium (PRM) was prepared from 1% glucose, 0.5% yeast extract, 0.5% casamino acids, 0.4M sucrose (as an osmostabillizer) and 2% agar.

100 μl samples containing $5 \times 10^7 - 1 \times 10^8$ spheroplasts were mixed with 3–5 μg of plasmid DNA (in less than 20 μl of 10 mM Tris-HCl, 1 mM EDTA pH 8.0) and incubated for 15 minutes at room temperature. Then, 1ml of 40% PEG 4000, 10 mM CaCl$_2$, 10 mM Tris-HCl pH 8.0 was added and the mixture incubated for an additional 15 minutes at room temperature. After recovering by low-speed centrifugation, spheroplasts were resuspended in 1 ml STC buffer, mixed with 5 mls of plasmid regeneration medium at 50° C. and plated onto regeneration plates containing 20 ml of PRM. After 24h incubation at 28° C., an additional 5 ml of top-agar containing enough G418 to give a final concentration of the antibiotic of 50 μg/ml was layered over. Plates were then incubated at 28° C. and, after 6–10 days, scored for transformants, which usually appear with a frequency of 0.5–1 transformant/μg DNA only in the plates corresponding to spheroplast samples that have been exposed to transforming plasmid DNA.

Colonies were picked up from the selective plates and transferred to flasks containing defined medium plus G418, where they grew after a 5–7 day incubation at 28° C. DNA isolated from these cultures by SDS-lysis and phenol extraction of spheroplasts was digested with restriction endonucleases. The resulting fragments were separated on agarose gel, denatured, transferred to nitrocellulose paper and hydridized with $^{32}$P-pMA4, usually to reveal that the DNA had been integrated in the recipient genome and did not appear as an autonomous replicon.

EXAMPLE 3

Preparation of pMA3

The low molecular weight, high copy number plasmid pCD5 (Scott et al. CELL 1983, 34 pg 557) which confers ampicillin resistance in *E. coli* was used as the basic replicon for in vitro constructions.

Figure 1:
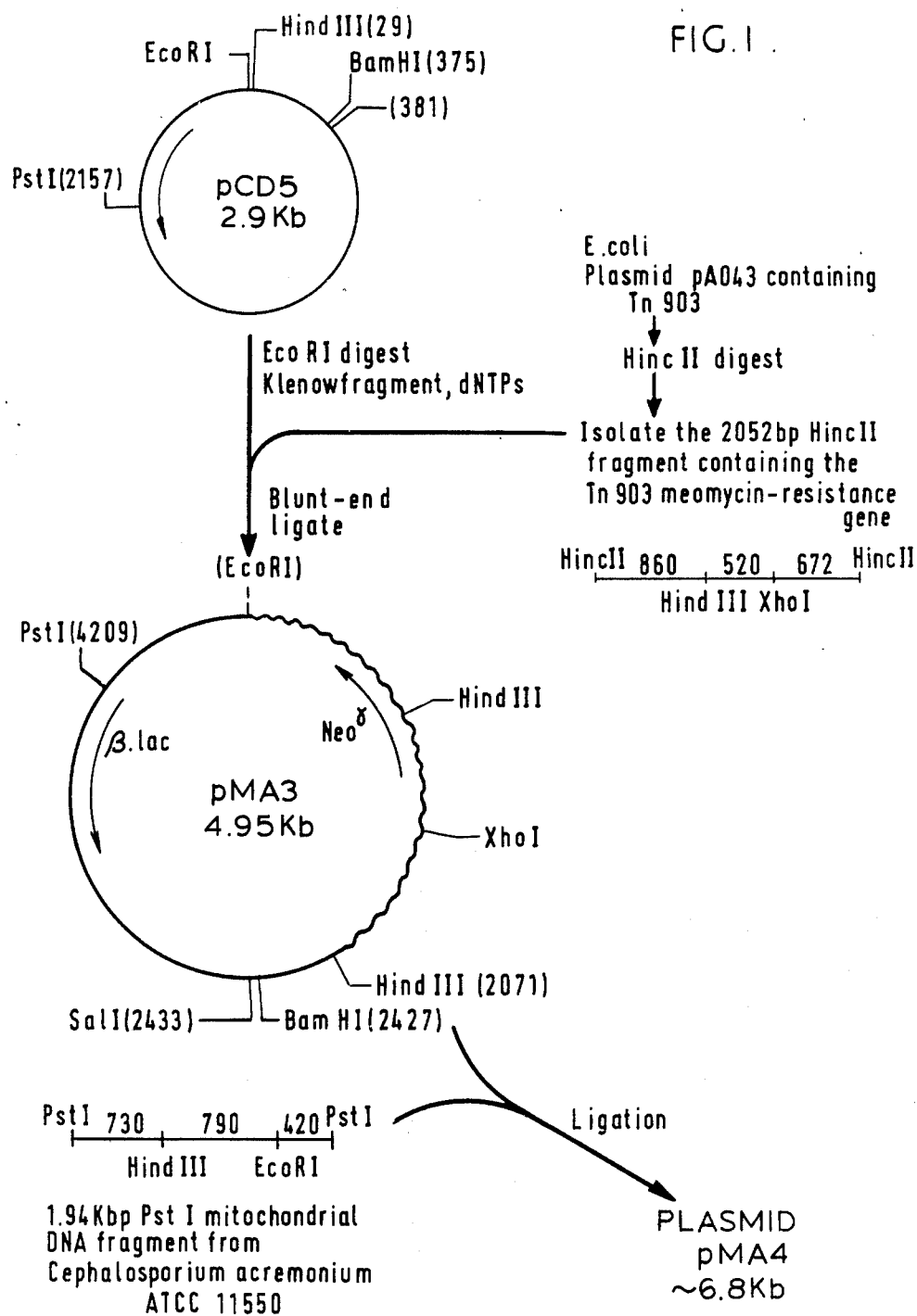
FIG. 1, shows a scheme for construction of plasmids pMA3 and pMA4.

As generally shown in FIG. 1, plasmid pCD5 was linearized at its single EcoRI site and the protruding ends were filled-in by incubation with the large (Klenow) fragment of *E. coli* DNA polymerase I and the four deoxyribonucleotide triphosphates. The resulting linear molecules were blunt-end ligated to a 2052 bp Hinc II fragment obtained by digestion of plasmid pA043 (Oka et al. already cited) with Hinc II. This fragment contains the entire coding region of the aminoglycoside phosphotransferase enzyme codified by the *E. coli* transposon Tn903 that confers neomycin resistance in *E. coli* and G418 resistance in yeast (Jimenez et al. already cited).

The ligation mixture was used to transform *E. coli* DH1 to neomycin resistance. Tranformants of the expected phenotype (neomycin-resistant, ampicillin-resistant) were screened for the presence of plasmids of the expected size. One clone containing a plasmid with one of the two possible orientations of the insert was selected and the plasmid, named pMA3 (see FIG. 1) was isolated.

EXAMPLE 4

Preparation of ARS Sequence

The autonomous replication sequence, ars, from mitochondrial DNA of *C. acremonium* is of considerable interest and utility. We have sequenced the 1.93 Pst I fragment, thereby opening up the possibility of further research and development. The full sequence for the 1.93 Pst I fragment is shown in FIG. 5.

The ars function does not extend over the whole fragment which we have sequenced. For example, the ars might constitute only a small percentage of the sequence shown in FIG. 5. The present invention extends to sequences which show substantial functional homology with that part of the sequence in which is the ars.

EXAMPLE 5

Preparation of pMA4

As further shown in FIG. 1, plasmid pMA3 was linearized at its single PstI site and ligated to the 1.93 Kb PstI fragment from the mitochondrial DNA of *C. acremonium* ATCC 11550. This fragment has been shown to contain an ars (autonomously replicating sequence) which is functional in yeast (P Tudzynski et al. and P Skatrud et al. already cited).

Figure 2:
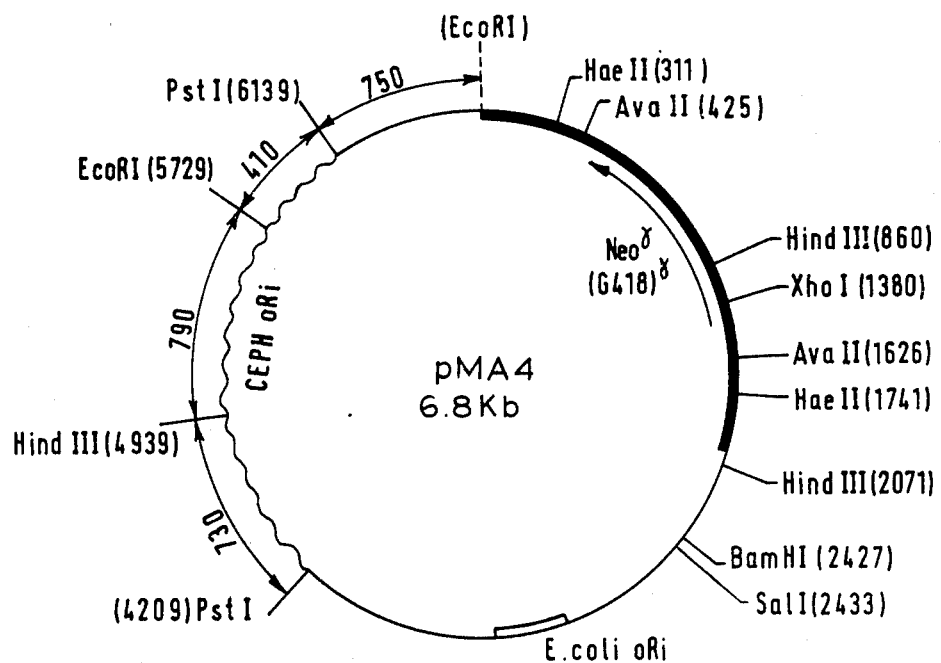
FIG. 2, shows a restriction enzyme map of plasmid pMA4.

The ligation mix was used to transform *E. coli* DH1 to neomycin-resistance and the resulting colonies were screened for ampicillin sensitivity. Plasmids isolated from colonies with the desired phenotype were analyzed by restriction enzyme mapping and a clone containing the 6.8 kb plasmid named pMA4 (FIG. 2) was selected.

The pMA4 was purified from large-scale culture and this plasmid was used to transform *E. coli* DH1. *E. coli* DH1/pMA4 has been deposited at the National Collection of Industrial and Marine Bacteria on Nov. 1, 1984 under the accession number NCIB 12025.

Thus, the plasmid pMA4 was constructed from three different DNA sequences, namely plasmid pCD5 (Scott et al., already cited), Tn903, and a 1.93 Pst I fragment containing an ars sequence from mitochondrial DNA of *C. acremonium* (P. Tudzynski et al., Curr. Genet., 2 (1982), 153 and P. Skatrud et al., Curr. Genet., 8 (1984), 155). The intermediate combination of plasmid pCD5 and Tn903 gave plasmid pMA3 which is useful in its own right as an origin-less plasmid with a single Pst I site. The plasmid can thus be employed for screening of ars-like sequences in *C. acremonium*.

Plasmids isolated from colonies with the desired phenotype were analyzed by restriction enzyme mapping and a clone containing the 6.8kb plasmid named pMA4. The pMA4 was purified from large-scale culture and this plasmid was used to transform *C. acremonium* to G418 resistance.

EXAMPLE 6

Preparation of cassette fragment

The plasmid pMA3 or pMA4 was digested with the restriction enzyme AvaII, the fragments were separated by acrylamide gel electrophoresis and the fragment containing the neomycin resistance gene was purified.

Figure 3:
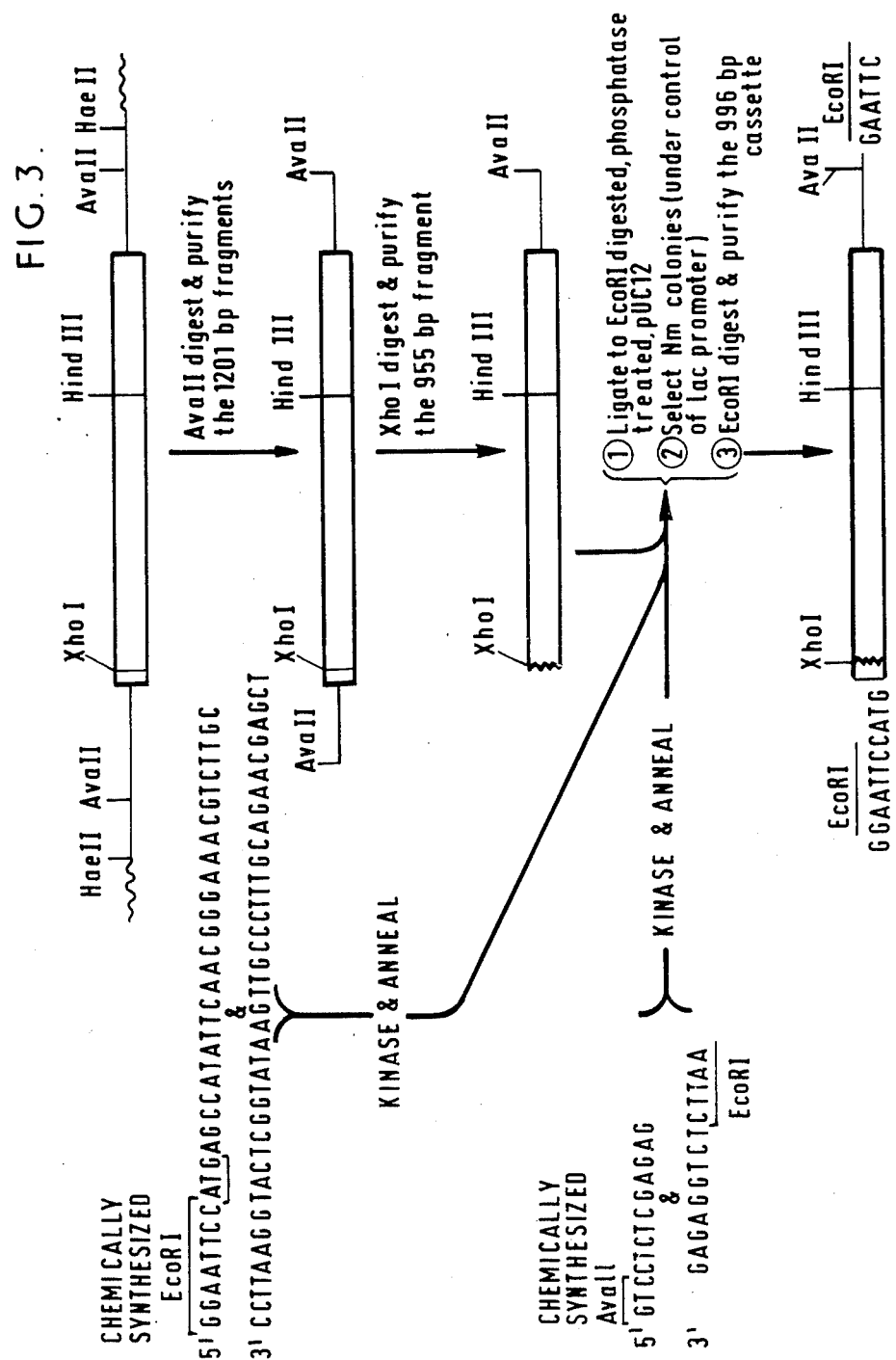
FIG. 3, shows a scheme for construction of a cassette fragment containing the Tn903 APH(3')-I sequence.

The next steps are outlined in FIG. 3. The purified AvaII fragment was digested with XhoI which cuts it at a single site, around 30 base pairs downstream of the initial ATG codon of the gene (thus deleting an essential part of it). The XhoI-AvaII fragment containing the major part of the gene was purified by acrylamide gel electrophoresis.

In order to restore the essential part of the gene and to provide a fragment with cohesive ends for easier cloning, two adapters were synthesized. Their sequences are as follows:

| |
|---|
| Adapter A: GGAATTCCATGAGCCATATTCAA |
| CGGGAAACGTCTTGC |
| CCTTAAGGTACTCGGTATAAGTTG |
| CCCTTTGCAGAACGAGCT |
| Adapter B: GTCCTCTCGAGAG |
| GAGAGCTCTCTTAA |

Adapter A has a cohesive end for XhoI and contains the coding sequence deleted from the gene, along with a recognition sequence for the enzyme EcoRI. Adapter B has two cohesive ends, one for AvaII and one for EcoRI. Adapter A was digested with EcoRI to generate a second cohesive end.

A mixture of the EcoRI-digested adapter A, adapter B, fragment XhoI-AvaII, and EcoRI-digested, phosphatase treated vector pUC12 [Messing, J.: New M13 Vectors for cloning, Methods in Enzymology, 101 (1983) 20–784] was incubated with T4 DNA ligase. The product was used to transform *E. coli* cells.

Neomycin-resistant colonies (which presumably expressed the gene under the control of the lac promoter present in vector pUC12) were selected. A plasmid from one of these clones was digested with EcoRI and a 996 base pair EcoRI fragment purified by acrylamide gel electrophoresis.

EXAMPLE 7

Preparation of pFS1 Fragment

Figure 4:
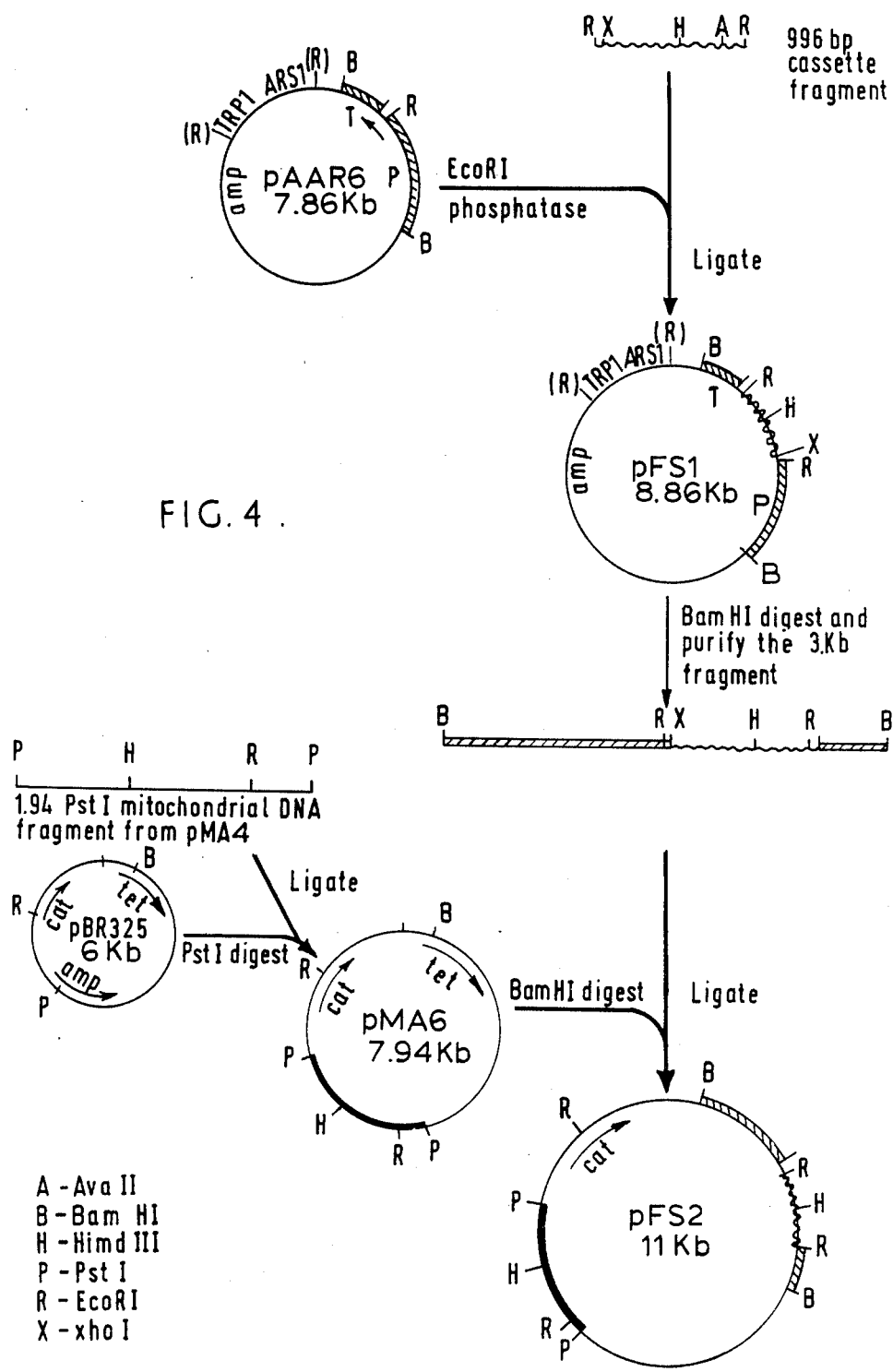
FIG. 4, shows a scheme for construction of plasmids pFS1, pMA6 and pFS2.

As shown in FIG. 4, plasmid pAAR6 [Ammerer, G.: Expression of genes of yeast using the ADCI promoter, Methods in Enzymology 101 (1983) 192–201] contains the promoter (P) and terminator (T) sequences of the ADCI gene coding for the alcohol dehydrogenase I of *Saccharomyces cerevisiae*. It has a single EcoRI cleavage site between the promoter and terminator which thus allows the insertion of a gene under the control of this promoter. A single BamHI or SphI fragment containing the sequence "promoter-inserted gene-terminator" can be rescued from the construction.

This type of fragment is of particular utility. The type of promoter and gene which may be employed are not limited to the (P) and (T) sequences of the *S. cerevisiae* alcohol dehydrogenase I gene.

As shown in FIG. 4, the EcoRI fragment containing the gene for APH(3')I of Tn903 was ligated to EcoRI-digested, phosphatase-treated pAAR6. *E. coli* cells were transformed with the mixture and colonies containing hybrid plasmids having the gene in the right orientation were selected. Such hybrid clones do not confer neomycin resistance to *E. coli* cells, probably due to the substitution in promoter. The plasmid pFS1 was isolated from such transformants, digested with BamHI and the 3 Kb fragment containing the gene (plus promoter and terminator) purified by acrylamide gel electrophoresis.

EXAMPLE 8

Preparation of pMA6 and pFS2

Plasmid pCD5 is not a convenient starting vector for putting the APH(3')I gene under the control of the ADCI promoter, as in a construction similar to pMA4 (which contains the 1.9 Kb PstI mitochondrial fragment). The difficulty with pCD5 is that its unique marker ($Ap^R$) is inactivated by the insertion of the $Nm^R$ gene and the new eukaryotic promoter would not allow the expression of the $Nm^R$ gene in *E. coli*, therefore resulting in a plasmid without a marker in *E. coli*.

Accordingly, the 1.9 Kb PstI mitochondrial DNA fragment was inserted at the PstI site within the $Ap^R$ gene of the known plasmid pBR325 ($Ap^R Tc^R Cm^R$) to give plasmid pMA6 ($Ap^s Tc^R Cm^R$), as shown in FIG. 4. BamHI-digested plasmid pMA6 was ligated to the 3 Kb BamHI fragment derived from pFS1, and *E. coli* cells were transformed with the resultant mixture. Colonies having the desired phenotype ($Ap^s Tc^s Cm^R$) with tetracycline sensitivity due to insertion of the fragment were selected. A clone containing the 11 Kb plasmid pFS2 was selected. Plasmid pFS2 was purified from large scale cultures and this plasmid was used to transform speroplasts of *Cephalosporium acremonium* to G418 resistance. The plasmid pFS2 allows increased growth rate of the Cephalosporium transformants on selection plates and consequently an easier distinction from spontaneous resistant clones.

Although the present invention has been hereinbefore described with particular reference to the manipulation of genes coding for antibiotic-inactivating enzymes, it should be understood that the invention extends to those systems in which the genes are of other types, such as those directing the synthesis of cephalasporin antibiotics or other eukaryotic genes of interest.

We claim:

1. *Cephalosporium acremonium* transformed with a vector comprising an aminoglycoside resistance marker which confers resistance to the aminoglycoside antibiotic G418.

2. *Cephalosporium acremonium* according to claim 1, wherein said resistance is provided by a gene coding for an aminoglycoside 3′-phosphotransferase.

3. *Cephalosporium acremonium* according to claim 2, wherein said gene is from the genome of *E. coli* containing transposon Tn601(903), transposon Tn5, or from the genome of *Streptomyces fradiae*.

4. *Cephalosporium acremonium* according to claim 2, wherein transcription of said gene is promoted by a eukaryotic promoter.

5. *Cephalosporium acremonium* according to claim 4, wherein said eukaryotic promoter comprises the promoter of *Saccharomyces cerevisiae* alcohol dehydrogenase I gene.

6. A method of selecting the transformed *Cephalosporium acremonium* of claim 1 from non-transformed cells of *Cephalosporium acremonium* comprising treating the cells with the aminoglycoside antibiotic G418 in an amount sufficient to select for resistant cells.

7. The plasmid pMA4 deposit number NCID 12025.

* * * * *